(12) United States Patent
Alvino et al.

(10) Patent No.: US 8,945,843 B2
(45) Date of Patent: Feb. 3, 2015

(54) THERMOCOOLER WITH THERMAL BREAKS THAT THERMALLY ISOLATE A THERMOCYCLING REGION FROM AT LEAST ONE GUARD HEAT REGION

(75) Inventors: Andrew Alvino, Haverhill, MA (US); John M. Cavacas, South Windsor, CT (US); Keith Crowe, Littleton, MA (US)

(73) Assignee: Analogic Corporation, Peabody, MA (US)

( * ) Notice: Subject to any disclaimer, the term of this patent is extended or adjusted under 35 U.S.C. 154(b) by 1091 days.

(21) Appl. No.: 12/964,193

(22) Filed: Dec. 9, 2010

(65) Prior Publication Data
US 2012/0149020 A1  Jun. 14, 2012

(51) Int. Cl.
*C12Q 1/68* (2006.01)
*C12P 19/34* (2006.01)
*C12M 1/00* (2006.01)
*B01L 7/00* (2006.01)

(52) U.S. Cl.
CPC .............. *B01L 7/52* (2013.01); *B01L 2200/147* (2013.01); *B01L 2300/1822* (2013.01); *C12Q 1/6869* (2013.01)
USPC .... 435/6.12; 435/91.2; 435/287.2; 435/289.1

(58) Field of Classification Search
USPC .......................... 435/6.12, 91.2, 287.2, 289.1
See application file for complete search history.

(56) References Cited

U.S. PATENT DOCUMENTS

| | | | |
|---|---|---|---|
| 5,302,347 A | 4/1994 | Van Den Berg et al. | |
| 6,180,372 B1 | 1/2001 | Franzen | |
| 6,428,987 B2 | 8/2002 | Franzen | |
| 6,613,560 B1 | 9/2003 | Tso et al. | |
| 2004/0241048 A1 | 12/2004 | Shin et al. | |
| 2007/0110634 A1* | 5/2007 | Heimberg et al. | 422/102 |
| 2007/0140926 A1* | 6/2007 | Heimberg et al. | 422/130 |
| 2010/0081191 A1 | 4/2010 | Woods | |

* cited by examiner

*Primary Examiner* — Kenneth Horlick
(74) *Attorney, Agent, or Firm* — Anthony M. Del Zoppo, III; Driggs, Hogg, Daugherty & Del Zoppo, Co. LPA

(57) ABSTRACT

A sample processing apparatus includes a sample carrier receiving region configured to receive a sample carrier carrying at least one sample, at least one sample processing station that processes the at least one sample, and a thermal control system that controls thermocycling of the sample during processing of the sample by the at least one sample processing station, wherein the thermal control system includes a heating and/or cooling substrate with a thermocycling region, at least one guard heat region, and at least one thermal break between the thermocycling region and the at least one guard heat region.

21 Claims, 4 Drawing Sheets

THERMOCOOLER WITH THERMAL BREAKS THAT THERMALLY ISOLATE A THERMOCYCLING REGION FROM AT LEAST ONE GUARD HEAT REGION

TECHNICAL FIELD

The following generally relates to thermocycling a sample in connection with processing the sample and is described with particular application to DNA sample processing such as DNA sequencing; however, the following is also amenable to other DNA sample processing and/or non-DNA sample processing.

BACKGROUND

A micro-channel device has been used to carry a small volume of a sample for processing and/or analysis. Processing of the sample has required thermocycling the sample through a plurality of different predetermined temperatures. By way of example, DNA sequencing has included replication of extracted and purified DNA fragments from a sample through a process called polymerase chain reaction (PCR), which requires rapid and precise thermocycling of the sample through three different temperatures. Temperature non-uniformity across the sample, at any of the predetermined temperatures, of more than one degree may inhibit suitable replication.

A thermoelectric cooler (TEC), or Peltier device, generally is a thermoelectric heat pump, which transfers heat from one side of the device to the other side of the device, and has been used in connection with DNA sequencing for thermocycling samples. In use, the device is placed in thermal communication with a DNA sample, and an appropriate voltage is applied across the device to create a temperature gradient for transferring heat between the sides of the device, either away from the sample to cool the sample or towards the sample to heat the sample. The polarity of the applied voltage determines whether the device heats or cools the sample.

Unfortunately, with a TEC device, heat may be lost (e.g., via convection and/or otherwise) to a greater degree at peripheral regions of the TEC device, relative to inner more central regions of the TEC device. Sources that may contribute to such heat loss include, but are not limited to, the ambient environment, a heat sink in thermal communication with the TEC device, and the device carrying the sample being thermocylced. This heat loss may lead to a dome-shaped temperature distribution or other temperature gradient across the surface of the TEC device and, hence, a dome-shaped temperature distribution across the sample. Moreover, over time, "hot" spots may form in peripheral regions of the TEC device, for example, due to induced thermal stress, leading to thermal drift, or a shift in the distribution of temperature across the TEC device.

Various approaches have been used in an attempt to improve temperature uniformity delivered by TEC devices. For example, a high conductivity heat spreader layer has been used in connection with TEC devices to reduce any temperature gradient. In yet another example, a thick, high thermal conductivity source plate has been used in connection with TEC devices to promote temperature uniformity. Unfortunately, these approaches pose other complications and/or additional costs.

SUMMARY

Aspects of the application address the above matters, and others.

In one non-limiting aspect, a sample processing apparatus includes a sample carrier receiving region configured to receive a sample carrier carrying at least one sample, at least one sample processing station that processes the at least one sample, and a thermal control system that controls thermocycling of the sample during processing of the sample by the at least one sample processing station, wherein the thermal control system includes a heating and/or cooling substrate with a thermocycling region, at least one guard heat region, and at least one thermal break between the thermocycling region and the at least one guard heat region.

In another non-limiting aspect, a method includes thermocycling a sample during processing of the sample using a heating and/or cooling substrate that includes a thermocycling region, at least one guard heat region, and at least one thermal break, wherein the at least one guard heat region and the at least one thermal break thermally isolates the thermocycling region.

In yet another non-limiting aspect, a DNA analyzer includes means for supporting a sample carrier carrying one or more DNA fragments in the DNA analyzer and means for providing substantially uniform temperature at each temperature during thermocycling of the DNA fragments under polymerase chain reaction based replication.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
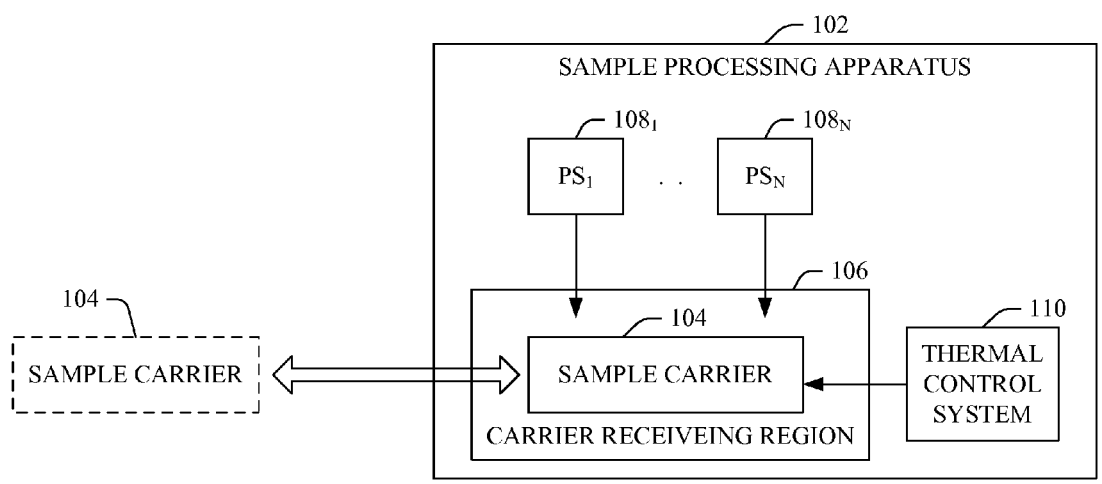
FIG. 1 illustrates an example sample processing apparatus, including a thermal control system for controlling thermocycling thereof.

FIG. 1 illustrates a sample processing apparatus 102 for processing, in parallel or in series, one or more samples located on a micro channel device such as a sample carrier 104. The illustrated embodiment is configured to simultaneously process multiple samples carried by the sample carrier 104. A non-limiting example of a suitable sample carrier is a biochip with one or more micro channels for bio-samples (e.g., blood, saliva, skin cells, etc.). In this instance, the sample processing apparatus 102 may be configured for DNA (e.g., sequencing), enzymatic, protein, and/or other processing and/or analysis. Other suitable carriers include, but are not limited to, a micro-channel device, a lab-on-a-chip, and/or other sample carrier.

The sample processing apparatus 102 includes a carrier receiving region 106 that is configured to receive the sample carrier 104. The carrier receiving region 106 supports a loaded sample carrier 104 for processing by the sample processing apparatus 102. The sample processing apparatus 102 further includes one or more processing stations ($PS_1, \ldots PS_N$) $108_1, \ldots, 108_N$ (wherein N is an integer equal to or greater than one), collectively referred to herein as processing stations 108, that process one or more samples of the sample carrier 104 loaded in the sample carrier receiving region 106.

In the context of processing samples including DNA, the illustrated processing stations 108 are configured to carry out at least one or more of the following: extraction/purification of DNA fragments from the sample, fragment labeling, fragment replication or amplification, and fragment separation (e.g., through electrophoresis). Replication generally is achieved through polymerase chain reaction (PCR), which includes concurrently thermal cycling multiple bio-samples rapidly and precisely between various uniformly distributed temperatures, for example, in a range from zero (0) degrees Celsius (° C.) to 100° C., such as between 56° C., 72° C., and/or 92° C., and/or other temperatures.

The sample processing apparatus 102 also includes a thermal control system 110 that controls thermocycling of the one or more samples carried by the sample carrier 104. As described in greater detail below, in one instance, the illustrated thermal control system 110 includes a thermoelectric cooler (TEC) device, such as a Peltier device or the like, with a thermally conductive surface having an inner heating and/or cooling sub-region (thermocycling region), which is thermally isolated via at least one peripheral heating and/or cooling sub-region (guard heat region) and a gap or material free region (thermal breaks) there between.

The inner heating and/or cooling sub-region provides a zone or generally central region of substantial temperature uniformity (e.g., less than one (1) degree of difference, or other predefined temperature difference). It is to be appreciated that such as zone may mitigate or reduce thermocycling temperature non-uniformity, for example, due to a greater loss of heat at the edges of the surface of the TEC device 202 in the peripheral sub-region(s), a change in temperature distribution across the surface of the TEC device in the peripheral sub-region(s), etc. As such, the thermal control system 110 is well-suited for applications in which temperature uniformity is desirable and/or needed such as thermocycling a DNA sample during replication via PCR.

Figure 2:
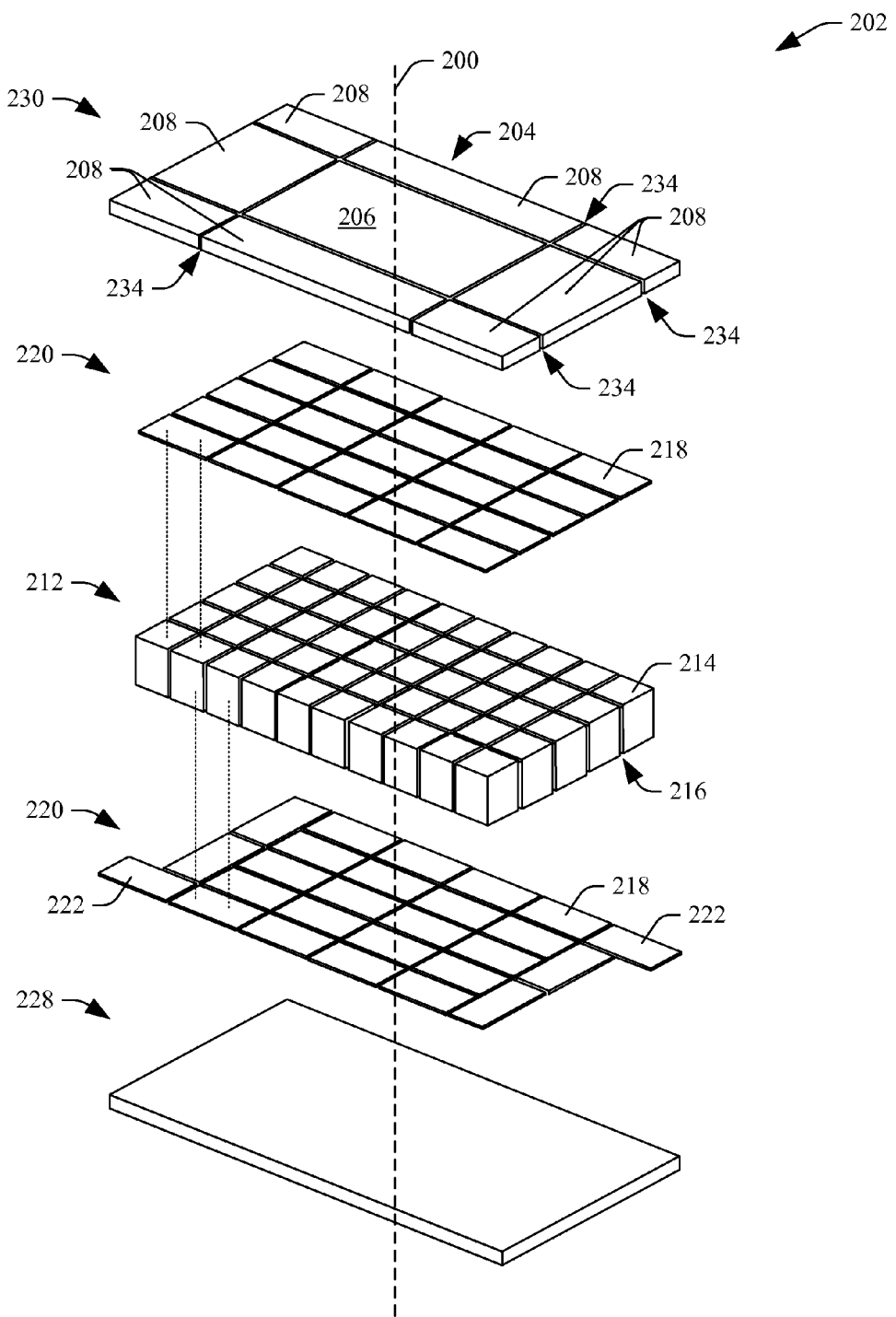
FIGS. 2-4 illustrate an example of a thermal control system including a heating and/or cooling substrate with a thermocycling region in thermal communication with the sample and thermally isolated from the ambient environment.
Figure 3:
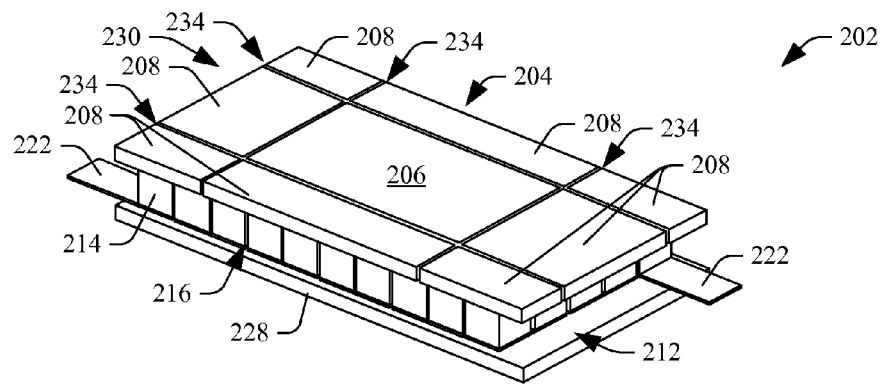
Figure 4:
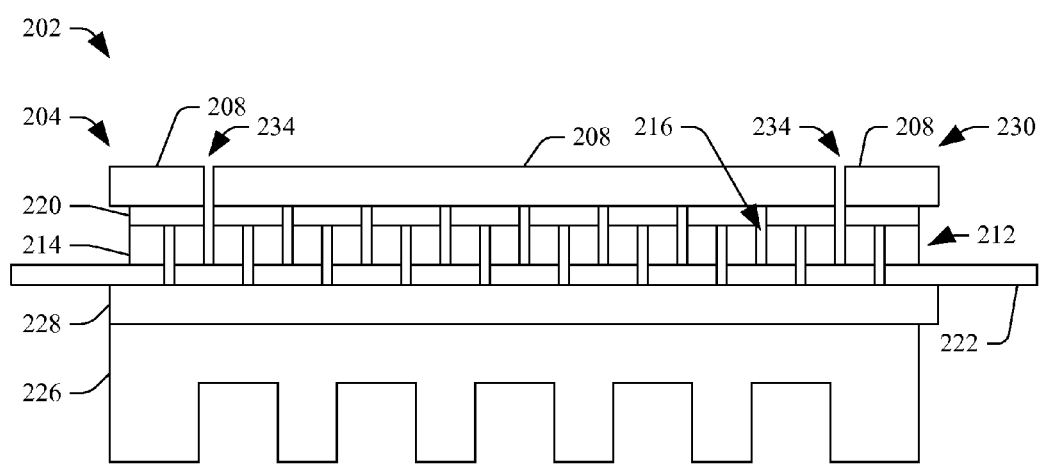

FIGS. 2, 3 and 4 illustrate an example of the thermal control system 110. In this example, the thermal control system 110 includes a TEC device 202 with a heating and/or cooling surface 204 with an inner heating and/or cooling sub-region 206, the one or more peripheral heating and/or cooling sub-regions 208, and the one or more gaps 234. For explanatory purposes, FIG. 2 shows the individual layers of the TEC device separated along an axis 200 generally perpendicular to the layers, FIG. 3 shows a perspective view the layers together, and FIG. 4 shows a side view with the layers together and a heat sink.

Generally, the TEC device 202 includes a matrix 212 of semi-conductor elements 214. Such elements may include Bismuth Telluride or other semi-conducting material, which is well-suited for pumping heat via electron ("N-type") and hole ("P-type") charge carriers. The individual semi-conductor elements 214 are arranged along rows and columns in an alternating manner based on semi-conductor type (N or P) such that an N-type element is followed by a P-type semi-conductor element 214, which is followed by an N-type semi-conductor element 214, . . . . The individual semi-conductor elements 214 are separated from each other by gaps or non-materials regions 216.

Matrices 220 of electrically conductive members 218 are respectively electrically coupled to pairs of different types (N and P) semi-conductor elements 214, forming electrically conductive junctions between the pairs of the semi-conductor elements 214, thereby forming an electrically conductive pathway through the semi-conductor matrix 212. The electrically conductive members 218 may include copper, silver, gold and/or other electrically conductive materials, and can be affixed to the semi-conductor elements 214 via solder or the like. In the illustrated embodiment, two of the electrically conductive members 218 include sub-portions 222 or tabs protruding from the TEC device 202 and configured for electrical connection with an electrical source such a direct current (DC), rectified alternating current (AC), and/or other source. Suitable voltages include voltages up to twenty-four (24) volts direct current (DC) or higher, and depend on the set of predetermined cycling temperatures, dissipation characteristics of the TEC device 202, etc.

With a positive voltage potential applied to the tab 222 in electrical communication with the P-type element 218 and a negative voltage potential applied to the tab 222 in electrical communication with the N-type element 218, the positive charge carriers (the holes) in the P material are repelled by the positive voltage potential and attracted by the negative pole, and the negative charge carriers (the electrons) in the N material are likewise repelled by the negative potential and attracted by the positive pole of the voltage supply, and electrons flow through the electrical pathway from negative to positive, moving or pumping heat from a bottom of the semi-conductor matrix 212 where the tabs 222 are located to a top of the semi-conductor matrix 212. Reversing the polarity causes the electrons to flow and heat to be moved in the opposite direction.

A bottom thermally conductive substrate 228 is affixed to the electrically conductive members 218 affixed to a bottom side of the semi-conductor matrix 212. In the illustrated embodiment, the bottom thermally conductive substrate 228 includes a thermally conductive material such as a ceramic (e.g., Alumina ceramic $Al_2O_3$, Beryllium Oxide BeO, Aluminum Nitride AlN, and/or other ceramic), a metal (where electrically isolated from the conductive members 218), and/or other thermally conductive substrate. Various approaches can be used to couple the substrate 228 and the electrically conductive members 218. By way of example, the substrate 228 can be affixed to the electrically conductive members 218 via solder between a metallization on the ceramic substrate 228 and the electrically conductive members 218.

A heat sink 226 (FIG. 3) is affixed to the bottom thermally conductive substrate 228 and facilitates heat transfer in the TEC device 202. The heat sink 226 may be affixed to the bottom thermally conductive substrate 228 via solder, glue, etc.

A top thermally conductive substrate 230 is substantially similar to the bottom thermally conductive substrate 228. As briefly noted above, the top thermally conductive substrate 230 includes the heating and/or cooling surface 204 which has the inner heating and/or cooling sub-region (thermocycling region) 206 (which forms a central heating and/or cooling region), the one or more peripheral heating and/or cooling sub-regions (guard heat region) 208, and the one or more gaps 234 (thermal breaks).

Various approaches can be used to physically create the gaps 234. By way of example, the peripheral sub-regions 208 can be physically separated from the inner heating and/or cooling sub-region 206 of the substrate 230 via dicing, for example, by cutting via a mechanical saw (e.g., diamond circular saw, wire saw, etc.), a laser, and/or other wafer dicing techniques substantially or entirely through the substrate 230, creating the gaps. In one instance, a gap 234 may be about six (6) mils wide (one hundred fifty (150) microns). Other gap widths are also contemplated herein. The gap 234 may be cut fully through the thickness of the substrate 230 (e.g., about 30 mils thick (seven hundred fifty (750) microns) or partially through to a point where the gap 234 behaves as a thermal barrier.

In the illustrated embodiment, the gaps 234 align with the outer gaps or non-materials regions 216 between the electrically conductive members 218 and the semi-conductor matrix 212. The gaps 234 are made only through the substrate 230, and such locations may facilitate making the gaps 234 without interrupting (e.g., opening) the electrically conductive members 218, and, hence the electrical pathway through the matrix 212. In other embodiments, the gaps 234 are made over the electrically conductive members 218. The one or more peripheral sub-regions 208 are thermally de-coupled or isolated from the inner heating/cooling region 206 in that the gaps 234 physically separate the one or more peripheral sub-regions 208 and the inner heating and/or cooling sub-region 206.

The inner heating and/or cooling region 206 forms a generally central zone of temperature uniformity for the TEC device 202, which may augment temperature uniformity of the sample. As such, the inner heating and/or cooling sub-region 206 may be less susceptible to temperature non-uniformity, for example, due to heat loss at the edges via heat conduction, relative to a configuration in which the substrate 230 does not include the peripheral sub-regions 208 and/or the gaps 234 The inner heating and/or cooling sub-region 206 is also less susceptible to thermal drift over time, or shifts in the distribution of temperature across the surface, for example, due to "hot" spots at the peripheral regions. The gaps 234 may also improve reliability of the TEC device 202.

A sealant, such as a non-electrically conductive and low thermally conductive sealant such as a silicone, epoxy, or the like can be applied around the open sides of the semi-conductive matrix 212 and/or in the gaps 234. The sealant may protect the TEC device 202 from the surrounding environment, mitigate trapping moisture in the matrix 212, etc.

The illustrated TEC device 202 is rectangular in shape. In other embodiments, the TEC device may be otherwise shaped such as square or other shape.

Variations are discussed.

FIGS. 5-10 show top down views, looking into top of the TEC devices 202.

Figure 5:
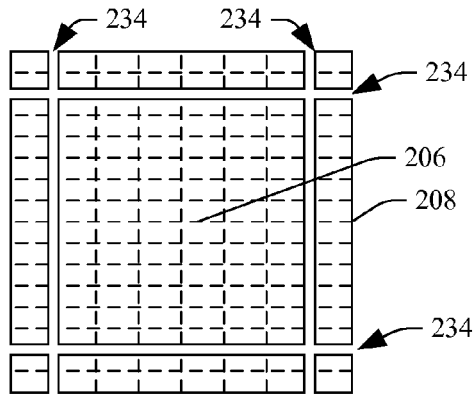
FIG. 5 illustrates an example of the heating and/or cooling substrate with a single level of thermal isolation for the thermocycling region.

In FIG. 5, the gaps 234 are located such that the one or more peripheral sub-regions 208 surround the inner heating and/or cooling sub-region 206 and are two semi-conductor elements 214 wide. Depending on the direction (x or y) along the substrate 230, the one or more peripheral sub-regions 208 may be one or more electrically conductive elements 218 wide. Generally, the number of conductive elements 218 in a segment is driven by the layout of the electrically conductive elements 218.

Figure 6:
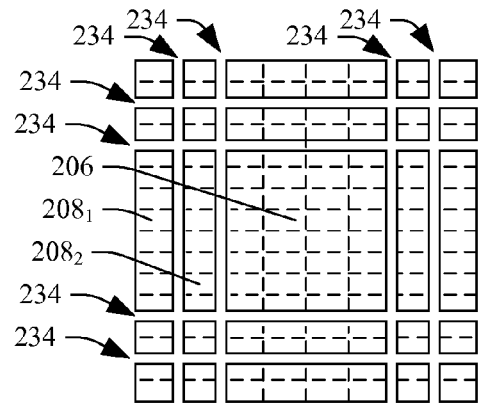
FIG. 6 illustrates an example of the heating and/or cooling substrate with two levels of thermal isolation for the thermocycling region.

Depending on a size of the TEC device 202, a required heating/cooling area, the circuit layout, etc., more than one level of thermal isolation region may be used. FIG. 6 shows the TEC device 202 with two levels of symmetrically positioned peripheral sub-regions 208, including an outer level $208_1$ and an inner level $208_2$, which is between the outer level and the inner heating and/or cooling sub-region 206. Of course, the TEC device 202 may include more than two levels. Additional interior cuts may be made to satisfy long term reliability requirements.

Figure 7:
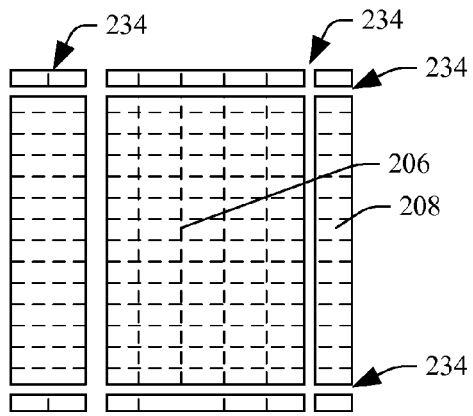
FIG. 7 illustrates an example of the heating and/or cooling substrate with asymmetric thermal isolation for the thermocycling region.

FIG. 7 shows an embodiment in which the gaps 234 are asymmetrically distributed, with different numbers of semi-conductor elements 214 included in the different sub-regions 208, depending on the direction (x or y) in the substrate 230.

Figure 8:
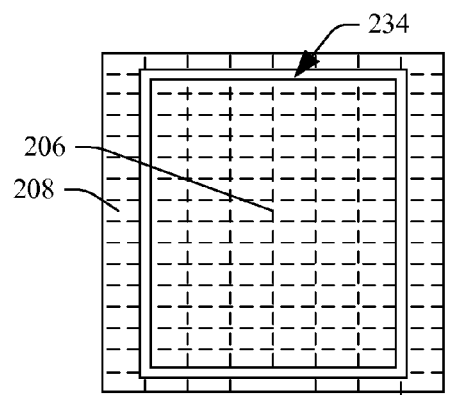
FIGS. 8, 9 and 10 illustrate various example thermal isolation patterns for the thermocycling region.

In FIGS. 5-7, the gaps 234 extend to the edges of the top thermally conductive substrate 230. In FIG. 8, the gaps 234 do not extend of the edges of the top thermally conductive substrate 230.

Figure 9:
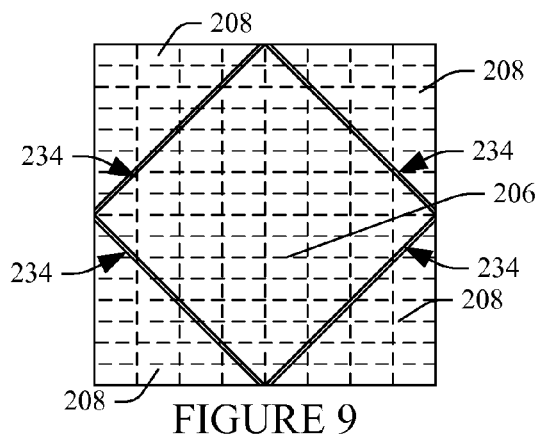

FIG. 9 illustrates an embodiment in which gaps 234 extend diagonally across the substrate 230, with respect to the gaps or non-materials regions 216 between the semi-conductor elements 214 of the semi-conductor matrix 212 and the electrically conductive members 218.

Although the TEC device 202 has been described herein in connection with DNA sequencing, it is to be appreciated that the TEC device 202 can be employed in connection with other applications in which a sample is thermocycled between temperatures, such as rapidly thermocycled between the temperatures, where temperature accuracy, precision, and uniformity is of interest.

Figure 10:
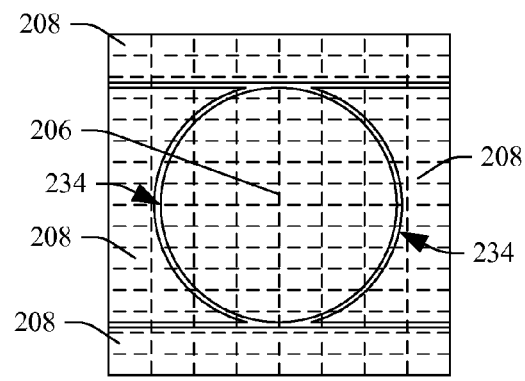

FIG. 10 illustrates an embodiment with semi-circular or circular shaped gaps 234.

Although the embodiments in FIGS. 2-11 show multiple gaps 234, it is to be appreciated that a suitable TEC device 202 may only include a single gap 234.

In another embodiment, the thermal isolation is achieved by assembling the TEC device 202 with individual or pre-cut ceramic segments, which are separated from each other by a gap, thus, obtaining a substantially similar TEC device 202 without making cuts in the TEC device 202.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A sample processing apparatus, comprising:
    a sample carrier receiving region configured to receive a sample carrier carrying at least one sample;
    at least one sample processing station that processes the at least one sample; and
    a thermal control system that controls thermocycling of the at least one sample during processing of the at least one sample by the at least one sample processing station, wherein the thermal control system includes:
    a thermoelectric cooler device; and
    a heating and/or cooling substrate affixed to the thermoelectric cooler device, wherein the heating and/or cooling substrate includes a thermocycling region, at least one guard heat region, and at least one thermal break between the thermocycling region and the at least one guard heat region, and wherein both the thermocycling region and the at least one guard heat region are affixed to the same thermoelectric cooler device.

2. The sample processing apparatus of claim 1, wherein the thermoelectric cooler includes a Peltier device.

3. The sample processing apparatus of claim 1, the heating and/or cooling substrate comprising:
    a surface which is placed in thermal communication with the sample, wherein a temperature across the surface is uniform for each of the temperatures of the thermocycling.

4. The sample processing apparatus of claim 3, wherein the temperature does not vary across the surface by more than one degree for a given thermocycling temperature.

5. The sample processing apparatus of claim 1, wherein the thermal control system concurrently cycles the temperature of the thermocycling region and the at least one guard heat region.

6. The sample processing apparatus of claim 5, wherein the at least one guard heat region and the at least one thermal break thermally isolates the thermocycling region.

7. The sample processing apparatus of claim 1, the thermoelectric cooler device, comprising:
- a matrix of semi-conductor elements arranged along rows and columns in an alternating manner based on semi-conductor type such that N-type element and a P-type semi-conductor element are interlaced and separated from each other by non-materials region gaps;
- a first matrix of electrically conductive members respectively electrically coupled to pairs of different N and P semi-conductor elements on a first side of the matrix of semi-conductor elements, forming electrically conductive junctions between the pairs of the N and P semi-conductor elements, and including a first protruding tab in electrical connection with an electrical source;
- a second matrix of electrically conductive members respectively electrically coupled to pairs of different N and P semi-conductor elements on a second opposing side of the matrix of semi-conductor elements, forming electrically conductive junctions between the pairs of the N and P semi-conductor elements, and including a second protruding tab in electrical connection with the electrical source;
- wherein the first tab, the first matrix, the matrix of semi-conductor elements, the second matrix, and the second tab provide an electrically conductive pathway through the matrix of semi-conductor elements, and
- wherein the at least one thermal break is located over a plurality of the gaps.

8. The sample processing apparatus of claim 6, wherein the thermocycling region is surrounded by the at least one guard heat region.

9. The sample processing apparatus of claim 6, wherein the heating and/or cooling substrate includes at least two levels of guard heat regions, including a first level and at least a second level, and the at least second level is disposed between the first level and the thermocycling region.

10. The sample processing apparatus of claim 6, wherein the at least one guard heat region and the at least one thermal break isolates the thermocycling region from loss of heat at least one edge of the thermocycling region.

11. The sample processing apparatus of claim 6, wherein the at least one thermal break thermally isolates the thermocycling region from a change in a temperature distribution across the at least one guard heat region.

12. The sample processing apparatus of claim 1, wherein the thermal control system cycles the temperature of the heating and/or cooling substrate between at least three different temperatures.

13. The sample processing apparatus of claim 1, wherein the thermal control system cycles the temperature of the heating and/or cooling substrate.

14. The sample processing apparatus of claim 1, wherein the thermal control system includes a heat pump.

15. The sample processing apparatus of claim 1, wherein the sample includes a DNA fragment undergoing DNA sequencing.

16. The sample processing apparatus of claim 1, wherein the processing includes replicating a DNA fragment via polymerase chain reaction.

17. A method, comprising:
- thermocycling a sample carrier carrying a sample during processing of the sample using a heating and/or cooling substrate that includes a thermocycling region, at least one guard heat region, and at least one thermal break, wherein the thermocycling region and the at least one guard heat region are affixed to a same thermoelectric cooler device, and wherein the at least one guard heat region and the at least one thermal break thermally isolates the thermocycling region from the at least one guard heat region.

18. The method of claim 17, wherein a temperature across a surface of the thermocycling region in thermal communication with the sample is uniform.

19. The method of claim 17, wherein the thermocycling region is surrounded by the at least one guard heat region.

20. The method of claim 17, wherein the thermocycling region is surrounded by two or more guard heat regions.

21. The method of claim 17, wherein the sample includes a DNA fragment undergoing DNA analysis.

* * * * *